United States Patent [19]
Hoshino et al.

[11] Patent Number: 5,250,428
[45] Date of Patent: Oct. 5, 1993

[54] L-GULONO-GAMMA-LACTONE-DEHYDROGENASE FOR PRODUCING VITAMIN C

[75] Inventors: Tatsuo Hoshino, Kamakura, Japan; Peter K. Matzinger, Rodersdorf, Switzerland; Setsuko Ojima, Fujisawa; Teruhide Sugisawa, Yokohama, both of Japan

[73] Assignee: Hoffmann-La Roche Inc., Nutley, N.J.

[21] Appl. No.: 761,140

[22] Filed: Sep. 17, 1991

[30] Foreign Application Priority Data

Sep. 17, 1990 [EP] European Pat. Off. ........... 90117842

[51] Int. Cl.$^5$ .................. C12N 9/04; C12P 17/16; C12P 17/06
[52] U.S. Cl. ................... 435/190; 435/118; 435/125
[58] Field of Search .............. 435/118, 125, 190

[56] References Cited

FOREIGN PATENT DOCUMENTS 207763  6/1986  European Pat. Off. .

OTHER PUBLICATIONS

Shigeoka, Shigeru et al., "The Effect of Illumination on the L-Ascorbic Acid Content in *Euglena gracilis z*," Agric. Biol. Chem. (43), pp. 2053-2058, 1979.
Nishiki et al., Arch. Biochem. Biophy., 175, 427-435, (1976).
Nishiki et al., Biochemistry, 21, 5076-5082, 1982.
Nishiki et al., Arch. Biochem. Biophy., 191, 479-486, 1978.
Bleeg et al., Dur. J. Biochem., 127, 391-396, 1982.
Shigeoka et al., Agric. Biol. Chem., 43, 2187-2188, (1979).

*Primary Examiner*—David M. Naff
*Assistant Examiner*—Jeffrey J. Sevigny
*Attorney, Agent, or Firm*—George M. Gould; George W. Johnston

[57] ABSTRACT

The present invention concerns a novel process for the microbiological manufacture of L-ascorbic acid from L-gulono-gamma-lactone, a process for preparing the enzyme being responsible for the microbiological oxidation of L-gulono-gamma-lactone, and said enzyme as a homogeneous protein, which is a L-gulono-gamma-lactone dehydrogenase.

1 Claim, 1 Drawing Sheet

L-GULONO-GAMMA-LACTONE-DEHYDROGENASE FOR PRODUCING VITAMIN C

The present invention concerns a process for the microbiological manufacture of L-ascorbic acid from L-gulono-gamma-lactone, a process for preparing the enzyme responsible for the microbiological oxidation of L-gulono-gamma-lactone, and said enzyme in purified form, i.e. as a homogeneous protein, which enzyme is a L-gulono-gamma-lactone dehydrogenase.

BACKGROUND OF THE INVENTION

The enzyme L gulono-gamma-lactone dehydrogenase (hereinafter referred to as GLDH) provided by the present invention catalyzes the oxidation of L-gulono-gamma-lactone to L ascorbic acid (vitamin C).

Certain enzymes which catalyze the oxidation of L-gulono-gamma-lactone (I) to L-ascorbic acid (II)

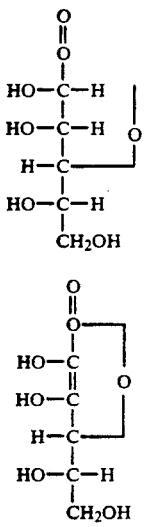

are known. Nishikimi et al. isolated L-gulono-gamma-lactone oxidase from rat liver (Arch. Biochem. Biophy., 175, 427–435, 1976), goat liver (Arch. Biochem. Biophy., 175, 427–435, 1976) and chicken kidney (Biochemistry, 21, 5076–5082, 1982). These enzymes consist of one subunit and use molecular oxygen as a direct electron acceptor in the oxidation of I to II. The GLDH of the present invention does not utilize molecular oxygen as a direct electron acceptor and consists of three kinds of subunits. Nishikimi et al. also isolated L-galactono-gamma-lactone oxidase from baker's yeast (Arch. Biochem. Biophy., 191, 479–486, 1978). This enzyme catalyzes the oxidation of both L-galactono-gamma-lactone and L-gulono-gamma-lactone to L-ascorbi acid. On the other hand, Bleeg et al. isolated L-galactono-gamma-lactone oxidase from Saccharomyces cerevisiae (Eur. J. Biochem., 127, 391–396, 1982). This enzyme was reported to be active on L-galactono-gamma-lactone, but not active on L-gulono-gamma-lactone. The GLDH of the present invention does not use L-galactono-gamma-lactone as a substrate.

Shigeoka et al. reported the characteristics of crude L-gulono-gamma-lactone dehydrogenase of Euglena gracilis z (Agric. Biol. Chem., 43, 2187–2188, 1979). The enzyme catalyzed the oxidation of both L-gulono-gamma-lactone and L-galactono-gamma-lactone, and was incapable of using oxygen as an electron acceptor. It is known that algac are difficult to handle due to the problems encountered with the growth of these microorganisms, e.g., fragility, cell division and the extended time periods involved.

There exists no report on the isolation of L-gulono-gamma-lactone dehydrogenase of Euglena gracilis z up to now. In addition, there have been no reports up to now on the conversion of L-gulono-gamma-lactone to L-scorbic acid using bacteria. According to the present invention, however, it has been found that bacteria are capable of producing L-ascorbic acid from L-gulono-gamma-lactone. This is the first possibility of such production of L-ascorbic acid from L-gulono-gamma-lactone using bacteria.

SUMMARY OF THE INVENTION

The present invention relates to the enzyme L-gulono-gamma-lactone dehydrogenase as a homogeneous enzyme, and a process for producing the enzyme. It has been found that the homogeneous enzyme, e.g. isolated from the soluble fraction of bacterial cells of specific microorganisms, catalyzes the oxidation of L-gulono-gamma-lactone to L-ascorbic acid. The present invention has been accomplished on the basis of this finding.

One of the objects of the present invention is to provide the GLDH as a homogeneous protein which acts on L-gulono-gamma-lactone to produce L-ascorbic acid. Another object of the present invention is to provide a process for producing the homogeneous GLDH by the cultivation of a microorganism, e.g. belonging to the genus Gluconobacter or a mutant thereof, which are capable of producing the GLDH in the cells, disruption of the cells, isolation and purification of it from the cell free extract of disrupted cells, preferably from the soluble fraction of microorganisms. A still further object of the present invention is to provide a process for producing L-ascorbic acid utilizing the GLDH. A further object is to provide a process for producing L-ascorbic acid by fermentation of bacteria. Moreover, a still further, object of the present invention is to provide the microorganisms having the GLDH activity. These and other objects will become more apparent from the description below.

DETAILED DESCRIPTION OF THE INVENTION

Figure 1:
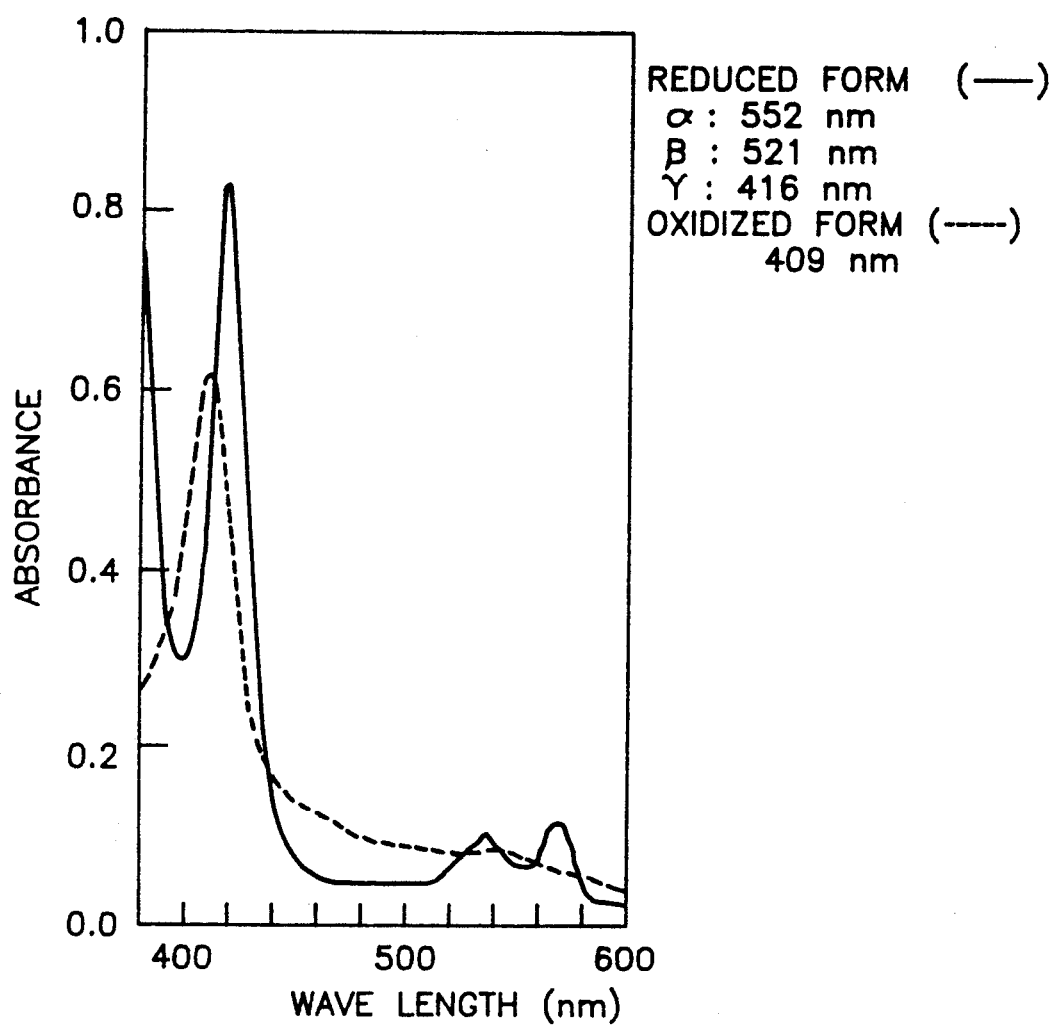
FIG. 1 shows the absorption spectra of L-gulono-gammalactone dehydrogenase.

The present invention pertains to the enzyme GLDH as a homogeneous protein, i.e., as a protein substantially free of other proteins, and to the preparation of the same. In addition, the present invention relates to a process for preparing L-ascorbic acid by oxidizing L-gulono-gamma-lactone in the presence of bacteria capable of producing the enzyme L-gulono-gamma-lactone dehydrogenase, a cell-free extract of the bacteria, or the soluble fraction of the bacteria, or the enzyme L-gulono-gamma-lactone dehydrogenase as a homogeneous protein, with the proviso that the oxidation takes place in the presence of an electron acceptor other than oxygen when the homogeneous enzyme is used.

The physico-chemical properties of the homogeneous GLDH, e.g. as exemplified below are as follows:

1) Enzyme activity:

The novel GLDH of the present invention catalyzes the oxidation of L-gulono-gamma-lactone to L-ascorbic acid in the presence of an electron acceptor according to the following reactions:

L-gulono-gamma-lactone + electron acceptor

L-ascorbic acid + reduced electron acceptor

The fact that the GLDH enzyme does not utilize oxygen as an electron acceptor was affirmed by the lack of enzyme catalyzing activity in converting L-gulono-gamma-lactone to L-ascorbic acid when oxygen is used as the electron acceptor. Furthermore, no oxygen consumption was detected in the reaction mixture using an oxygen probe. However, any conventional compound which has the ability to act as an electron acceptor can be utilized in conjunction with the enzyme of this invention for converting L-gulono-gamma-lactone to L-ascorbic acid. Any conventional electron acceptor, a coenzyme, or a compound exibiting such coenzyme function, e.g. 2.6-dichlorophenolindophenol (hereinafter referred to as DCIP), phenazinc methosulphate, Wurster's blue, ferricyanide, coenzyme Q, or cytochrome c, etc. can be used in the process of the present invention.

The enzyme assay was performed at 25° C. by measuring the decrease of absorbance at 600 nm of DCIP spectrophotometrically. One unit of enzyme activity was defined as the amount of enzyme which catalyzed the reduction of 1 $\mu$mole of DCIP per minute. The extinction coefficient of DCIP at pH 7.0 was taken as 14.5 mM$^{-1}$. A cuvette with 1 cm light path contained 0.16 mM DCIP, 1.6 mM phenazine methosulfate, 200 mM potassium phosphate buffer, 400 mM L-gulono-gamma-lactone, enzyme solution and water in a final volume of 0.5 ml. A reference cuvette contained all components except L-gulono gamma-lactone. The reaction was started by the addition of L-gulono-gamma-lactone. Enzyme activity was measured as the initial reduction rate of DCIP.

2) Substrate specificity:

Substrate specificity of the enzyme was determined using the same enzyme assay method as described as above except that the various substrate solutions (400 mM) were used instead of L-gulono-gamma-lactone. The results of the measurement are shown in Table 1. The GLDH is highly active on L-gulono-gamma-lactone and D-xylose and weakly active on D-glucuronogamma-lactone, D-glucose and D-mannose.

3) Optimum pH:

The correlation between the reaction rate of the GLDH and pH was determined using the same enzyme assay method as described under 1) except that various pH's buffers were used. The results are shown in Table 2. The enzyme showed the highest activity in a pH range between 7.0 and 8.0.

4) pH stability:

The enzyme as a homogeneous protein was kept standing in buffers of various pH for 192 hours at 4° C. The residual activity was measured using the same enzyme assay method as described under 1. The results of the measurement are shown in Table 3. The enzyme as a homogeneous protein was relatively stable at any pH between 6.5 and 9.2.

5) Heat stability:

The enzyme as a homogeneous protein was treated for 5 minutes at various temperatures in 200 mM potassium phosphate buffer (pH 7.0), and then cooled immediately in ice water. The residual activity was measured using the same enzyme assay method as described under 1). The results are shown in Table 4. The homogeneous enzyme was stable up to 30° C., and lost about 50 and 80% of its activity after incubation at 55° and 60° C., respectively.

6) Optimum temperature:

The enzyme activities of GLDH were measured at temperature from 25° to 55° C. by the same enzyme assay method as described under 1). The results are shown in Table 5. The enzyme did not have a distinct optimum temperature in the range tested.

7) Molecular weight:

The molecular weight of the GLDH was determined by high performance liquid chromatography using a size exclusion gel column (TSK gel G3000 SWxL column, 7.8 mm×30 cm) equilibrated with 100 mM potassium phosphate buffer (pH 7.0) containing 300 mM sodium chloride. As molecular weight standards, cyanocobalamin (M.W. 1,350), myoglobin (M.W. 17,000), ovalbumin (M.W. 44,000), gamma-globulin (M.W. 158,000) and thyroglobulin (M.W. 670,000) were used. The molecular weight of the GLDH was determined to be 110,000±2000.

Next, subunit-components of the purified GLDH were determined. The purified GLDH was treated by sodium dodecyl sulfate (hereinafter referred to as SDS) in the presence of beta-mercaptoethanol, and applied on the same column as described above equilibrated with 100 mM sodium phosphate buffer (pH 7.0) containing 0.1% SDS. As molecular weight standards, lysozyme (M.W. 14,000), soy bean trypsin inhibitor (M.W. 21,500), carbonic anhydrase (M.W. 31,000), ovalbumin (M.W. 45,000), bovine scrum albumin (M.W. 66,200) and phosphorylase B (M.W. 92,500) were used. The enzyme consists of three subunits whose molecular weights were 61,000, 32,500 and 16,500. The sum of these molecular weights is 110,000, the total molecular weights of native GLDH.

The largest component (M.W. 61,000) is probably a flavoprotein, since upon gel electrophoresis in SDS it showed intense fluorescence when the unstained gel was exposed to ultraviolet light. The second component (M.W. 32,500), which was stained by heme staining, is a cytochrome.

The third compound (M.W. 16,500±500) is a simple protein, i.e. a protein carrying no prostethic group. To sum up, the respective molecular weights are 61,000±1,000

32,500±1,000

16,500±500, the standard deviations having been established by conventional means, e.g. SDS electrophoresis.

The home staining of the above electrophoresis gel was carried out according to the procedure described by P. E. Thomas et al. in Analytical Biochemistry 75, 168–176 (1976), which can be summarized as follows:

A 6.3 mM 3,3',5,5'-tetramethylbenzidine (TMBZ) solution was freshly prepared in methanol. Immediately before use, 3 parts of the TMBZ solution were mixed with 7 parts of 0.25M sodium acetate, pH 5.0. The gel was immersed into this mixture at room temperature in the dark for 2 hours with occasional mixing. H$_2$O$_2$ was added to a final concentration of 30 mM to stain the second protein component including a cytochrome.

8) Absorption spectrum:

The absorption spectrum of the homogeneous GLDH reduced with sodium dithionite showed maxima at 416, 521 and 552 nm in the visible region, indicating the presence of a cytochrome c component, as shown in FIG. 1.

9) Measurement of the Km value:

Using the same enzyme assay method as described above, the rate of the oxidizing reaction with varying the concentrations of L-gulono-gamma lactone from 0.18 mM to 90 mM was measured to determine the Km value for L-gulono-gamma-lactone. The maximum reaction rate was found at the substrate concentration of about 71.8 mM. The apparent Michaelis constant (Km) was calculated to be 34.8 mM with DCIP as the electron acceptor.

10) Effect of metal ions:

Using the same enzyme assay method as described under 1), the effect of various metal ions on the enzyme activity was examined. The results are shown in Table 6. $Cu^{2+}$ and $Mn^{2+}$ showed strong inhibition of the enzyme.

11) Effect of inhibitors:

Using the same enzyme assay method as described above, the effect of various inhibitors on the enzyme activity was examined. The results are shown in Table 7. No compounds tested gave an inhibitory effect on the GLDH.

12) Purification method:

Purification of L-gulono-gamma-lactone dehydrogenase is effected by the combination of known purification methods, such as ion exchange chromatography, liquid chromatography, adsorption chromatography, gel-filtration chromatography, gel-electrophoresis, salting out and dialysis.

The microorganism used include all strains belonging to the genus Gluconobacter, showing good growth when cocultured in the presence of *Bacillus megaterium*. Mutants and variants of said microorganism can be also used in the present invention. The preferred strain is Gluconobacter oxydans.

The strains have been denominated and classified as Gluconobacter oxydans by reference to Bergey's Manual of Determinative Bacteriology, 8th edition, 1974, and, in particular, in view of the fact that they exhibit the following characteristics:

a) 2-keto-L-gulonic acid is produced from L-sorbose, b) ethanol is oxidized to acetic acid, c) D-glucose is oxidized to D gluconic acid and 2-keto-D-gluconic acid, d) ketogenesis of polyalcohols, e) pellicle and ring growth in mannitol broth (24 hours cultivation) at pH 4 and 5, and pellicle growth in D-glucose broth at pH 4.5.

In addition, they exhibit the following properties:

f) dihydroxyacetone is not substantially produced from glycerol, g) 2-keto-D-glucaric acid is produced from D-sorbitol and D glucaric acid, but not from D-glucose, D-fructose, D-gluconic acid, D-mannitol or 2-keto-D-gluconic acid, h) polymorphic, no flagella observed, i) a brown pigment is produced from D-fructose, j) good growth when co-cultured in the presence of *Bacillus megaterium* or a cell extract thereof, k) streptomycin sensitive.

A specific and preferred Gluconobacter oxydans strain has been deposited at the Deutsche Sammlung von Mikroorganismen in Goettingen under DSM 4025 on Mar. 17, 1987.

The cells of the Gluconobacter oxydans strain are rodshaped with round ends. The diameter of a cell of the Gluconobacter oxydans strain is, on the average, about 0.3–0.6 μm, its length about 0.9–1.6 μm, mainly 1–1.5 μm.

For the preparation of the GLDH, the microorganism may be cultured in an aqueous medium supplemented with appropriate nutrients under aerobic conditions. The cultivation may be conducted at a pH between about 4.0 and 9.0, preferably between about 6.0 and 8.0. While the cultivation period varies depending upon pH, temperature and nutrient medium used, usually 2 to 5 days will bring about favorable results. A preferred temperature range for carrying out for the cultivation is from about 13° to 36° C., more preferably from about 18° to 33° C.

It is usually required that the culture medium contains such nutrients as assimilable carbon sources, digestible nitrogen sources and inorganic substances, vitamins, trace elements and other growth promoting factors. As assimilable carbon sources, L-sorbose, glycerol, D-glucose, D-mannitol, D-fructose, D-arabitol and the like can be used. Various organic or inorganic substances may also be used as nitrogen sources, such as yeast extract, meat extract, peptone, casein, corn steep liquor, urea, amino acids, nitrates, ammonium salts and the like. As inorganic substances, magnesium sulfate, potassium phosphate, ferrous and ferric chlorides, calcium carbonate and the like may be used.

In the following, an embodiment for the preparation of homogeneous GLDH from microorganisms after cultivation is described.

(1) Cells are harvested from the fermentation broth by centrifugation or filtration.

(2) The cells are suspended in the buffer solution and disrupted by means of a homogenizer, sonicator or treatment with lysozyme and the like, to give a solution of disrupted cells.

(3) The GLDH is isolated and purified from cell free extract of disrupted cells, preferably from the soluble fraction of microorganisms.

In these steps, one preferably makes use of column chromatography, e.g.

1) DEAE cellulose column chromatography.
2) Q-Sepharose column chromatography,
3) Hydroxylapatite column chromatography,
4) Sephacryl S-300 column chromatography,
5) polyacrylamide gel electrophoresis, etc.

The GLDH of the present invention is useful as a catalyst for the production of L-ascorbic acid from L-gulono-gamma-lactone. This reaction should be conducted at pH values of from about 6.0 to 9.0 in the presence of an electron acceptor, for example, DCIP, PMS, Wurster's blue, ferricyanide, coenzyme Q, cytochrome c and the like, in a solvent such as McIlvaine buffer, potassium phosphate buffer, Tris-HCl buffer and the like.

A preferred temperature range for carrying out the reaction is from about 25° to 55° C. When the pH and the temperature are set at about 7.0–8.0 and 30°–50° C., respectively, the reaction usually brings about the most preferable results. Concentration of L-gulono-gamma-lactone as substrate in a solvent varies depending on other reaction conditions, but, in general, is desirable to be about 10–150 g/l, most preferably from about 10–100 g/l.

For this reaction, the enzyme may also be used in an immobilized state with an appropriate carrier. Any means of immobilizing enzyme generally known to the art may be used. For instance, the enzyme may be bound directly to a membrane, granules or the like of a resin having functional groups(s), or it may be bound through bridging compounds having bifunctional group(s), for example, glutaraldehyde, to the resin.

In as far as the fermentation process is concerned, the following parameters apply and the process is suitably done according to the following procedure respectively; a microorganism with the capability to produce II is cultivated in a nutrient aqueous solution in presence of compound I or is, after its growth, brought into contact with I in a buffer solution and then further incubated.

Any microorganism capable of producing the enzyme L-gulono-gamma-lactone dehydrogenase is suitable for use in the present invention. As examples of various microorganisms suitable for use in the present invention are the microorganisms listed below, and those microorganisms having the identifying characteristics of those listed below, or mutants or variants thereof:

Bacteria, e.g. of the genus;
Acetobacter, e.g. *Acetobacter suboxydans* (DSM 5935) [date of deposit: May 5, 1990], *Acetobacter oxydans* (DSM 5936)[May 5, 1990], *Acetobacter melanogenus* (NCIMB 8086) Gluconobacter, e.g. *Gluconobacter oxydans* (ATCC 621), *Gluconobacter oxydans* (DSM 4025).

Further suitable bacteria are: e.g.
Actinomyces, e.g. of the genus Streptomyces, such as *Streptomyces antibioticus* (ATCC 8633), *Streptomyces eurocidicus* (ATCC 19551), *Streptomyces lavendulae* (DSM 5926) [May 5, 1990], *Streptomyces olivaceus* (ATCC 3335), *Streptomyces netropsis* (NRRL 2268).
[NRRL=Northern Utilization Research and Development Division of U.S.D.A., Peoria, Ill., U.S.A. ATCC=American Type Culture Collection, Rockville, Md., U.S.A. NCIMB=National Collection of Industrial+Marine Bacteria, Torry Research Station, Aberdeen AB 9 8DG, Scotland DSM=German Collection of Microorganisms and Cell Cultures, Braunschwoig]

Specially preferred for the reaction are species of the genus Acetobacter and Gluconobacter, especially the aforementioned strains of Acetobacter suboxydans and Gluconobacter oxydans.

It is understood that every microorganism used according to the invention should preferably be grown in a nutrient medium before it is used for the inventory fermentation process. Its growth is possible in aqueous medium.

The nutrient medium with the grown microorganism can be used directly for the fermentation reaction.

The composition of the inventive reaction medium can be much simpler, e.g. a solution of educt I combined with the separately grown microorganisms in a buffer solution without any further additions.

The pH of the medium should preferably be between 2 and 9, preferably ca. 4–7. If desired the pH value may be adjusted by a buffer system.

For optimal yields it is preferable to use the educt in a concentration between ca. 1 and ca. 10% (per weight).

The preferable fermentation time is between 2 and 100 hours, especially between 4 and 72 hours. A feeding of educt I may prolong the fermentation time.

It is understood that the oxidation represents an aerobic process. These conditions are fulfilled with vivid shaking or stirring of the reaction medium under air or under additional aeration.

The following examples illustrate the present invention.

EXAMPLE 1

Preparation of L-gulono-gamma-lactone dehydrogenase as a homogeneous protein (1) Cultivation of Gluconobacter oxydans DSM 4025

Gluconobacter oxydans DSM 4025 was grown on an agar slant medium containing mannitol 5.0%, $MgSO_4.7H_2O$ 0.25%, corn steep liquor 1.75%, baker's yeast 5.0%, urea 0.5%, $CaCO_3$ 0.5% and agar 2.0% at 27° C. for 4 days. One loopful of the agar slant culture of Gluconobacter oxydans DSM No. 4025 was inoculated into 50 ml of a seed culture medium containing L-sorbose 8.0%, glycerol 0.05%, urea 0.5%, $MgSO_4.7H_2O$ 0.25%, corn steep liquor 1.75%, baker's yeast 5.0% and $CaCO_3$ 1.5% in a 500 ml-Erlenmeyer flask, and cultivated at 30° C. for 1 day on a rotary shaker (180 rpm). Five ml of this culture were transferred into 50 ml of the same medium in a 500 ml-Erlenmeyer flask, and cultivated in the same manner as described above. Two liters of the seed culture thus prepared were used as an inoculum for a 30 l-jar fermentor containing 20 liters of medium containing L-sorbose 8.0%. glycerol 0.05%, urea 1.2%, $MgSO_4.7H_2O$ 0.25, corn steep liquor 3.0%, baker's yeast 5.0% and $CaCO_3$ 1.5%. The jar fermentor was operated at 30° C., with 400 rpm agitation and 0.5 vvm (volume of air/volume of medium/minute), for aeration. After 40 hours fermentation, the cultured broth was centrifuged at 1,500 rpm for 10 minutes to remove calcium carbonate, then at 8,000 rpm (10,000×g) to pellet the cells. The cell cake was washed with 0.85% NaCl solution once. From 20 liters of the broth, about 100 g (wet weight) of the cells were obtained.

(2) Preparation of the soluble fraction

The cells of Gluconobacter oxydans DSM 4025 (95 g, wet weight) from the above step (1) were washed with 0.85% NaCl solution twice. The washed cells were suspended in 380 ml of 10 mM potassium phosphate buffer (pH 7.0), and the cell suspension was homogenized with a French press homogenizer at 1,500 kg/cm2. Cell debris was removed by centrifugation at 1.800×g for 10 minutes, and then the supernatant (hereinafter referred to as cell free extract) was centrifuged at 100,000×g for 60 minutes. minutes. The resulting supernatant (450 ml) was collected as the soluble fraction of the cells of Gluconobacter oxydans DSM 4025.

(3) Diethylaminoethyl (hereinafter referred to as DEAE)cellulose column chromatography The soluble fraction (450 ml) obtained in the previous step was dialyzed against 10 mM potassium phosphate buffer (pH 7.0). The dialysate (500 ml) was applied to a DEAE-cellulose column (2.5×120 cm), equilibrated with 10 mM potassium phosphate buffer (pH 7.0). The column was washed with the same buffer and then with the same buffer containing 0.25 M NaCl. The GLDH was eluted with the same buffer containing 0.5 M NaCl.

(4) Q-Sepharose column chromatography

The pooled active fraction (200 ml) from the previous step was dialyzed against two batches of 2 liters of 10 mM potassium phosphate buffer (pH 7.0), and applied to a Q-Sepharose column (2.5×50 cm) equilibrated with the same buffer. After the column was washed with the same buffer, the GLDH was eluted with the linear gradient of NaCl from 0.3M to 0.5M.

(5) Hydroxylapatite (Bio-gel HTT) column chromatography

The pooled active fraction (210 ml) from the previous step was dialyzed against two batches of 2 liters of 10 mM potassium phosphate buffer (pH 7.0), and applied on a hydroxyl apatite column (2.5×25 cm) equilibrated with the same buffer. The column was washed with the same buffer, and the GLDH was eluted with the linear gradient of potassium phosphate buffer (pH 7.0) from 10 mM to 40 mM. Fractions having enzyme activity were combined and concentrated to about 20 ml by ultrafiltration using a ultrafilter (pM10, Amicon).

(6) Sephacryl S-300 column chromatography

A portion of the enzyme fraction (2 ml) from the previous step was applied on Sephacryl S-300 column (1.0×100 cm) equilibrated with 50 mM potassium phosphate buffer (pH 7.0) containing 50 mM NaCl, and developed with the same buffer. The fractions containing electrophoretically homogeneous GLDH were combined and stored at $-80°$ C.

Using the purification steps as described above, the GLDH was purified about 900-fold. Summary of the purification steps of GLDH is shown in Table 8.

(7) Purity of the isolated homogeneous enzyme

To estimate the purity of the GLDH isolated, a polyacrylamide gel electrophoresis (separation gel: 10% polyacrylamide; conditions of electrophoresis: 20 mA at 4° C. for 6 hours) was performed. The enzyme yielded a single band stained by Coomassie brillant blue R-250. The protein band showed GLDH activity when the unstained gel was immersed in 50 mM potassium phosphate buffer (pH 7.0) containing 50 mM L-gulono-gamma-lactone, 20 μg/ml of nitroblue tetrazolium and 40 μg/ml of phenazine methosulfate for 20 minutes.

(8) Identification of the reaction product

The reaction mixture containing 0.5 ml of the homogeneous GLDH (7.5 μg, 469 units/mg protein), 1.0 ml of 0.5M potassium phosphate buffer (pH 7.0), 0.1 g of L-gulono-gamma-lactone, 0.1 ml of 10 mM phenazine methosulfate, and water in a final volume of 2.0 ml was incubated for 2 hours at 30° C. The reaction product was analyzed by both thin layer chromatography and high performance liquid chromatography. Thin layer chromatography was done as follows: a sample (1 μl) was spotted on a silica gel plate (Merck, U.S.A.), developed with a solvent system of n-propanol-water-1% phosphoric acid-formic acid (400:100:10:1) at room temperature for 2 hours. The plate was then dried and observed under an ultra-violet lamp. The product was found as UV-absorption spot at a Rf value of about 0.7 that corresponded with an authentic sample of L-ascorbic acid. High performance liquid chromatography was done as follows: a sample was applied on a LiChrosorb NH₂ column (Merck, U.S.A., 0.4×25 cm) equilibrated with a solvent system of acetonitrile-water-acetic acid 87:11:2. The flow rate was set at 3.0 ml/min, and the detection of products was made at 254 nm. As a result, the product eluted at the same retention time as an authentic sample of L-ascorbic acid.

Consequently, the product was identified to be L-ascorbic acid.

The productivity of L-ascorbic acid was 0.71 g/l/hour.

EXAMPLE 2

L-Ascorbic acid production from L-gulono-gamma-lactone by fermentation (growing cell).

A 200 ml of the seed culture of Gluconobacter oxydans DSM 4025 prepared in the same manner as described in Example 1-(1) was used to inoculate 2 liters of medium, which contained L-gulono-gamma-lactone 8%, glycerol 0.05%, baker's yeast 5.0%, MgSo$_4$.7H$_2$O 0.25%, corn steep liquor 1.75%, urea 0.5% and CaCO$_3$ 1.5% (the initial pH set at 7.0), in a 3-l jar fermentor. Fermentation was conducted at 30° C., 700 rpm for agitation and 0.5 vvm for aeration. As shown in Table 9, 8.6 g/l of L-ascorbic acid was produced in 66 hours of fermentation.

EXAMPLE 3

L-Ascorbic acid production from L-gulono-gamma-lactone under a resting cell system.

The cells of Gluconobacter oxydans DSM 4025 prepared in the same manner as described in Example 1-(1), 0.1 g to 0.67 g, were added into 50 mM potassium phosphate buffer (pH 7.0) containing 47.6 mg/ml or 89.3 mg/l of L-gulono-gamma-lactone in a total volume of 3 ml. The reaction mixture was incubated for 6 hours at 30° C. with shaking (280 rpm). The results are shown in Table 10. The highest productivity of L-ascorbic acid was 20 mg/hour/g-cells. And the highest yield of L-ascorbic acid was 13.92 g/l.

EXAMPLE 4

L-Ascorbic acid production from L-gulono-gamma-lactone using the cell free extract of Gluconobacter oxydans DSM 4025.

The reaction mixture containing 1.0 ml of cell free extract (protein content: 10.3 mg/ml) of Gluconobacter oxydans DSM 4025, as prepared in the same manner as described in Example 1-(1) and (2), 1 ml of 0.5M potassium phosphate buffer (pH 7.0) and 0.5 ml of 17.8% L-gulono-gamma-lactone was incubated at 30° C. for 17.5 hours. As a result, 2.19 g/l of L-ascorbic acid was produced.

EXAMPLE 5

L-Ascorbic acid production from L-gulono-gamma-lactone by fermentation (growing cell system) of Acetobactor Suboxydans (DSM 5935).

The bacterium Acetobacter suboxydans (DSM 5935) is grown on an agar slant in medium 1 (composition: 50% yeast water, 5% mannit, in tap water adjusted to pH 6.5). After 2 days incubation at 30° C. one loopful of cells are used to inoculate 5 ml liquid medium 1 (the same composition as described above but without agar). The tube is shaken at 30° C. with 220 rpm for 3 days. 1 ml preculture is used to inoculate 100 ml medium 1 together with 1 g of educt I. The flasks are shaken at 30° C. with 220 rpm. The process was terminated after 72 hours. According to the analytical determinations 3% educt I have been converted into product II.

EXAMPLE G

L-Ascorbic acid production from L-gulono-gamma-lactone under a resting cell system using Acetobacter Suboxydans (DSM 5935).

The bacterium Acetobacter suboxydans (DSM 5935) is grown as described above. The 100 ml cultures are harvested by centrifugation (10,000 rpm, 10 min.) and frozen in plastic vials above liquid nitrogen. 100 ml flasks with medium 1 are inoculated with 0.5 ml each from the vials, shaken at 30° C. at 220 rpm and 1 g educt I is added at the same time. According to the analytical determinations 10% of the educt I is transformed into product II within 72 hours.

EXAMPLE 7

L-Ascorbic acid production from L-gulono-gamma-lactone under a resting cell system using Acetobacter Suboxydans (DSM 5935).

The bacterium Acetobacter suboxydans (DSM 5935) is grown as described in Example 6. The 100 ml cultures, inoculated with 0.5 ml from the vials serve as preculture for another growth culture in the same medium. These flasks with 100 ml medium 1 are inoculated with 5 ml preculture and shaken for 24 hours at 30° C. with 220 rpm. The grown cells are harvested by centrifugation (10,000 rpm, 10 min.). 3 g of wet cells (corresponds to cells from one flask) are suspended in a buffer solution (pH 6.0, 0.05M phosphate buffer) together with 0.1 g of educt I (added as powder) in a total volume of 10 ml. 30% of educt I is transformed within 48 hours into product II.

EXAMPLE 8

L-Ascorbic acid production from L-gulono-gamma-lactone under a resting cell system using Acetobacter Suboxydans (DSM 5935).

The bacterium Acetobacter suboxydans (DSM 5935)) is grown on agar slants as described in Example 1. The layer of grown cells is suspended in 10 ml of a physiological NaCl solution (0.9%). This suspension is used to inoculate 10 shake flasks (100 ml medium 1) with 1 ml each. The flasks are incubated for 4 days at 30° C. with 220 rpm. The 10 cultures are used to inoculate a 10 lt blade-stirred bioreactor (9,000 ml medium 1). Growth conditions: temperature: 30° C., aeration 0.4 vvm, stirring 500 rpm. After 44 hours of growth the cells are harvested by centrifugation (continuous centrifugation with 12,000 rpm). The yield was 21 g wet cells per liter. The cells are deep frozen in portions. In the example 1 g of the frozen cells is thawed quickly and added together with 0.4 g educt I to 0.05M phosphate buffer of pH 7.0. The total volume of the assay mixture was 5 ml. According to analytical determinations 19% of I were transformed into product II.

TABLE 1

Substrate Specificity of L-Gulono-r-lactone Dehydrogenase

| Substrate | Relative activity (%) |
|---|---|
| L-Gulono-r-lactone | 100 |
| L-Galactono-r-lactone | 0 |
| D-Glucurono-r-lactone | 6.38 |
| D-Glucono-δ-lactone | 0 |
| D-Glucuronic acid | 0 |
| D-Gluconic acid | 0 |
| D-Glucose | 23.4 |
| D-Mannose | 7.23 |
| D-Galactose | 0 |
| L-Gulose | 0 |
| D-Xylose | 110.6 |

TABLE 2

Optimum pH of L-Gulono-r-lactone Dehydrogenase

| pH value | Relative activity (%) Buffers | | |
|---|---|---|---|
| | McIlvain | Potassium phosphate | Tris-HCl |
| 4.0 | 0 | — | — |
| 4.5 | 0 | — | — |
| 5.0 | 8.2 | — | — |
| 5.5 | 18.2 | — | — |
| 6.0 | 58.5 | — | — |
| 6.5 | 77.8 | 56.4 | — |
| 7.0 | 100 | 83.6 | 45.9 |
| 7.5 | 105.8 | 102.3 | 58.2 |
| 8.0 | 109.3 | — | 61.7 |
| 8.5 | — | — | 60.0 |

(—: not determined)

TABLE 3 pH Stability of L-Gulono-r-lactone Dehydrogenase

| pH value | Relative activity (%) Buffers | | | |
|---|---|---|---|---|
| | McIlvaine | Potassium phosphate | Tris-HCl | NH4OH—NH4Cl |
| 4.0 | 0 | — | — | — |
| 4.5 | 0 | — | — | — |
| 5.0 | 0 | — | — | — |
| 5.5 | 9.38 | — | — | — |
| 6.0 | 48.4 | 62.5 | — | — |
| 6.5 | 75.0 | 50.3 | — | — |
| 7.0 | 79.7 | 71.9 | 84.4 | — |
| 7.5 | 100 | 95.3 | 75.0 | — |
| 8.0 | 84.4 | — | 62.5 | — |
| 8.3 | — | — | 53.2 | 57.8 |
| 8.85 | — | — | — | 115.6 |
| 9.2 | — | — | — | 100 |
| 9.7 | — | — | — | 68.8 |

TABLE 4

Temperature Stability of L-Gulono-r-lactone Dehydrogenase

| Temperature (°C.) | Relative activity (%) |
|---|---|
| 0 | 100 |
| 25 | 100 |
| 30 | 100 |
| 35 | 89.6 |
| 40 | 87.5 |
| 45 | 72.9 |
| 50 | 70.8 |
| 55 | 53.1 |
| 60 | 18.8 |
| 65 | 0 |
| 70 | 0 |
| 75 | 0 |

TABLE 5

Optimum Temperature of L-Gulono-r-lactone Dehydrogenase

| Temperature (°C.) | Relative activity (%) |
|---|---|
| 25 | 100 |
| 30 | 103.2 |
| 35 | 101.8 |
| 40 | 106.6 |
| 45 | 101.4 |
| 50 | 115.1 |

TABLE 5-continued

Optimum Temperature of L-Gulono-r-lactone Dehydrogenase

| Temperature (°C.) | Relative activity (%) |
|---|---|
| 55 | 102.7 |

TABLE 6

Effect of Various Metals on L-Gulono-r-lactone Dehydrogenase

| Metal | Concentration (mM) | Relative activity (%) | Metal | Concentration (mM) | Relative activity (%) |
|---|---|---|---|---|---|
| $Ca(NO_3)_2.4H_2O$ | 0.19 | 100 | $MgSO_4.7H_2O$ | 0.19 | 92 |
|  | 0.38 | 100 |  | 0.38 | 96 |
|  | 0.89 | 96 |  | 0.89 | 92 |
| $CaCl_2$ | 0.19 | 96 | $MgCl_2.6H_2O$ | 0.19 | 96 |
|  | 0.38 | 104 |  | 0.38 | 96 |
|  | 0.89 | 96 |  | 0.89 | 96 |
| $CoCl_2.6H_2O$ | 0.19 | 102 | $MnCl_2.4H_2O$ | 0.19 | 100 |
|  | 0.38 | 110 |  | 0.38 | 0 |
|  | 0.89 | 100 |  | 0.89 | 0 |
| $CoSO_4.7H_2O$ | 0.19 | 96 | $MnSO_4.4-6H_2O$ | 0.19 | 100 |
|  | 0.38 | 108 |  | 0.38 | 0 |
|  | 0.89 | 88 |  | 0.89 | 0 |
| $CuSO_4$ | 0.19 | 92 | $Na_2MoO_4.2H_2O$ | 0.19 | 104 |
|  | 0.38 | 24 |  | 0.38 | 96 |
|  | 0.89 | 12 |  | 0.89 | 88 |
| $CuSO_4.5H_2O$ | 0.19 | 80 | TiCl | 0.19 | 88 |
|  | 0.38 | 20 |  | 0.38 | 92 |
|  | 0.89 | 0 |  | 0.89 | 80 |
| $Cu(NO_3)_2.3H_2O$ | 0.19 | 88 | $ZnCl_2$ | 0.19 | 88 |
|  | 0.38 | 24 |  | 0.38 | 88 |
|  | 0.89 | 0 |  | 0.89 | 80 |
| $CuCl_2.2H_2O$ | 0.19 | 84 | $ZnSO_4.7H_2O$ | 0.19 | 88 |
|  | 0.38 | 8 |  | 0.38 | 88 |
|  | 0.89 | 0 |  | 0.89 | 76 |
| $Fe(SO_4)_3.xH_2O$ | 0.19 | 104 | $NiSO_4.7H_2O$ | 0.19 | 96 |
|  | 0.38 | 92 |  | 0.38 | 96 |
|  | 0.89 | 76 |  | 0.89 | 88 |
| $K_4Fe(CN)_6.3H_2O$ | 0.10 | 0 | None |  | 100 |

TABLE 7

Effect of Various Inhibitors on L-Gulono-r-lactone Dehydrogenase Activity

| Inhibitor | Concentration (mM) | Relative activity (%) |
|---|---|---|
| EDTA | 0.96 | 95.2 |
|  | 1.89 | 100 |
|  | 4.46 | 90.5 |
| N-Ethyl-maleimide | 0.96 | 95.2 |
|  | 1.89 | 100 |
|  | 4.46 | 100 |
| Sodium azide | 0.96 | 100 |
|  | 1.89 | 97.6 |
|  | 4.46 | 97.6 |
| Monoiodoacetate | 0.96 | 104.8 |
|  | 1.89 | 100 |
|  | 4.46 | 92.9 |
| PCMB (p-chloro-mercuribenzoate) | 0.96 | 90.5 |
|  | 1.89 | 102.4 |
|  | 4.46 | 100 |
| $Na_2HAsO_4 7H_2O$ | 0.96 | 95.2 |
|  | 1.89 | 104.8 |
|  | 4.46 | 97.6 |
| Sodium fluoride | 0.96 | 107.1 |
|  | 1.89 | 114.3 |
|  | 4.46 | 97.6 |
| KCN | 0.96 | 96.0 |
|  | 1.89 | 96.0 |
|  | 4.46 | 96.0 |
| Hydroxylamine hydrocloride | 1.0 | 100 |
|  | 2.0 | 100 |
| Hydrazine monohydrate | 1.0 | 100 |
| None |  | 100 |

TABLE 8

Summary of Purification Steps of L-Gulono-r-lactone Dehydrogenase

| Step | Total activity (units) | Total protein (mg) | Specific activity (units/mg) | Recovery (%) |
|---|---|---|---|---|
| Soluble fraction | 1179.9 | 2289.5 | 0.52 | 100 |
| DEAE Cellulose | 766.9 | 66.44 | 11.54 | 65.0 |
| Q Sepharose | 761.8 | 8.65 | 88.10 | 64.6 |
| Hydroxylapatite | 473.1 | 3.24 | 146.0 | 40.1 |
| Sephacryl S-300 | 37.8 | 0.0806 | 469.0 | — |

TABLE 9

L-Ascorbic Acid Production from L-Gulono-r-lactone by Fermentation

| Cultivation time (hour) | L-Ascorbic acid produced (g/l) |
|---|---|
| 0 | 0.0715 |
| 18.5 | 3.54 |
| 27 | 5.12 |
| 42 | 6.96 |
| 51 | 7.88 |
| 66 | 8.57 |
| 75 | 8.46 |
| 90 | 7.72 |

TABLE 10

L-Ascorbic Acid Production from L-Gulono-r-lactone by Resting Cell System

| Initial L-gulono-r-lactone concentration (mg/ml) | Cell concentration (g cell wet weight/ml) | L-Ascorbic acid produced (ng/ml) at 3 hr | at 6 hr |
|---|---|---|---|
| 0 | 0.1 | 0 | 0 |
| 47.6 | 0.1 | 5.98 | 7.22 |
|  | 0.17 | 6.46 | 7.82 |
|  | 0.33 | 7.83 | 9.65 |
|  | 0.67 | 9.51 | 11.28 |
| 89.3 | 0.1 | 5.88 | 7.62 |
|  | 0.17 | 6.88 | 9.50 |

TABLE 10-continued

L-Ascorbic Acid Production from L-Gulono-r-lactone
by Resting Cell System

| Initial L-gulono-r-lactone concentration (mg/ml) | Cell concentration (g cell wet weight/ml) | L-Ascorbic acid produced (ng/ml) | |
|---|---|---|---|
| | | at 3 hr | at 6 hr |
| | 0.33 | 8.37 | 13.92 |
| | 0.67 | 8.67 | 13.51 |

What is claimed is:

1. An essentially pure L-gulono-gamma-lactone-dehydrogenase having the following properties:
   a) a high substrate specificity with L-gulono-gamma lactone and D-xylose;
   b) an optimum pH of about 7 to about 8;
   c) a molecular weight of $110,000 \pm 2,000$ consisting of three subunits, the subunits comprising a flavoprotein prosthetic group having a molecular weight of $61,000 \pm 1,000$, a cytochrome c protein having a molecular weight of $32,500 \pm 1,000$, and a simple protein having a molecular weight of $16,500 \pm 500$; and
   d) inhibition by the metal ions $Cu^{2+}$ and $Mn^{2+}$.

* * * * *